United States Patent [19]

Snyder et al.

[11] Patent Number: 5,047,318

[45] Date of Patent: Sep. 10, 1991

[54] IMIDAZOLE LEUCO DYE COMPOSITION CONTAINING 4'-HYDROXYACETANILIDE, DIAGNOSTIC KIT AND METHOD USING SAME

[75] Inventors: Brian A. Snyder, Rochester; Harold C. Warren, III, Rush, both of N.Y.; Gregory J. McClune, Portage, Mich.

[73] Assignee: Eastman Kodak Company, Rochester, N.Y.

[21] Appl. No.: 206,258

[22] Filed: Jun. 13, 1988

[51] Int. Cl.[5] .................. G01N 33/53; G01N 33/543; C12Q 1/34; C12Q 1/28

[52] U.S. Cl. .......................... 435/5; 435/7.9; 435/7.92; 435/18; 435/28; 435/971; 435/7.36; 436/501; 436/518; 436/535; 436/538; 436/543; 436/544; 436/547; 436/824; 422/56

[58] Field of Search .............. 435/7, 18, 5, 27, 28, 435/177, 180, 810, 188, 7.1, 7.9, 7.92, 967, 971, 7.36; 436/501, 518, 527, 530, 800, 808, 823, 535, 538, 543, 544, 547, 824; 526/264, 303, 317; 528/422, 425; 548/346; 422/56

[56] References Cited

U.S. PATENT DOCUMENTS

| | | | |
|---|---|---|---|
| 4,089,747 | 5/1978 | Bruschi | 195/99 |
| 4,283,491 | 8/1981 | Dappen | 435/14 |
| 4,424,150 | 6/1984 | Khanna | 260/112 |
| 4,504,413 | 3/1985 | Khanna | 260/112 |
| 4,746,607 | 5/1988 | Mura et al. | 435/25 |
| 4,828,983 | 5/1989 | McClune | 435/17 |

FOREIGN PATENT DOCUMENTS 0122641 10/1984 European Pat. Off. .

OTHER PUBLICATIONS

U.S. Ser. No. 884,329, filed 7/10/86 by McClune; corresponding E.P. Publication 252,747.

Primary Examiner—Esther L. Kepplinger
Assistant Examiner—Florina B. Hoffer
Attorney, Agent, or Firm—J. Lanny Tucker

[57] ABSTRACT

A dye-providing composition is useful in various diagnostic assays wherein a peroxidase-labeled specific binding species is used. This composition is substantially free of peroxidase and such labeled species, and comprises an imidazole leuco dye and 4'-hydroxyacetanilide present in an amount up to about 2.5 mmolar. This composition can be included as part of a diagnostic test kit.

8 Claims, No Drawings

IMIDAZOLE LEUCO DYE COMPOSITION CONTAINING 4'-HYDROXYACETANILIDE, DIAGNOSTIC KIT AND METHOD USING SAME

FIELD OF THE INVENTION

This invention relates to a dye-providing composition comprising an imidazole leuco dye and a specific amount of 4'-hydroxyacetanilide. It also relates to a diagnostic test kit including the composition. The invention is useful in diagnostic methods.

BACKGROUND OF THE INVENTION

There is a continuing need in medical practice, research and diagnostic procedures for rapid and accurate detection or quantification of biological and chemical substances which are present in biological fluids, cells or tissues. For example, the presence of drugs, hormones, steroids, polypeptides, nucleotides, prostaglandins, proteins, carbohydrates or infectious organisms (bacteria, fungi or viruses) in biological specimens has to be determined in an accurate and rapid fashion for suitable diagnosis or treatment.

For example, organisms classified as gram positive bacteria, such as group specific Streptococcus, are known to be pathogenic in humans. For instance, Group A organisms are primarily responsible for causing B-hemolytic pneumonia, scarlet fever, rheumatic fever, cardiac sequelae, glomerulonephritis, septic sore throat and puerpueral sepsis. Because of the serious nature of infections potentially caused by Streptococcus A, it is important to diagnose its presence at an early stage so that an appropriate course of treatment can be pursued. In most cases, the diagnostic tests require several hours, or at least up to 30 minutes. Even this limited wait may be intolerable in many instances where the practitioner has many waiting patients, and the patients themselves can not wait for the diagnosis without considerable cost, inconvenience or discomfort.

To provide diagnostic determinations, various methods have been devised for isolating and identifying biological or chemical substances employing specific binding reactions between the substance to be detected (identified as a "target ligand" or simply "ligand" herein) and receptors (molecules which specifically react or bind with that substance). This reaction between a ligand and its corresponding receptor is known as a specific binding reaction. Where either the ligand or receptor is an antibody, the reaction is known as an immunological reaction. More than one ligand or receptor may participate in each reaction.

Such reactions are detected in a number of ways. Generally, one or more participants of the specific binding reaction is detectably labeled. That is, it is either chosen because it is inherently detectable, or a detectable moiety (for example, an enzyme, radioisotope, chromogen or fluorogen) is incorporated therein in some manner. Many assays (for example, ELISA) today utilize enzymes as detectable moieties because of the convenience they provide in requiring minimum equipment and skills needed for the assays, as well as improved sensitivity in some cases.

Copending and commonly assigned U.S. Ser. No. 206,257, filed on even date herewith by Warren III and Snyder and entitled "Specific Binding Composition Comprising a Low pI Protein or Carbohydrate and a Diagnostic Test Kit and Method of Use" describes the use of a low pI protein with a specific binding species to reduce assay background without affecting sensitivity. This advance in the art greatly improves the assay. However, it has been found that further sensitivity is needed in addition to low background for the assay to effectively detect low amounts of ligand. This is especially critical where the ligand is a pathogen and early detection of disease is urgently needed.

Copending and commonly assigned U.S. Ser. No. 884,329 (filed July 10, 1986 by McClune) describes the use of a phenol or aniline in combination with peroxidase or a peroxidase-labeled ligand analog and a leuco dye. The phenol or aniline (such as 4'-hydroxyacetanilide) is used as a electron transfer agent to accelerate the formation of dye. At least 0.001 mmolar, and preferably 0.1 to 10 mmolar phenol or aniline is used in the composition. This application teaches that 4'-hydroxyacetanilide or other phenols will increase the rate of dye formation from leuco dyes so that the assay is more rapid. As more of the phenol is used, the more rapid the rate of dye formation. Moreover, the phenol and leuco dye are used in combination with a peroxidase-labeled ligand because of the nature of the assays described therein.

Generally, high concentrations of peroxidase-labeled antibody are needed to detect low concentrations of antigen in an assay. Higher concentrations are also conventionally used to achieve maximum complexing kinetics and to provide sufficient enzyme to maximize the overall kinetics of dye formation for a rapid and sensitive assay. Unfortunately, these higher concentrations of labeled antibody give higher background levels which can adversely affect sensitivity. Background is unwanted dye signal which is not the result of the presence of antigen.

Moreover, when the concentration of 4'-hydroxyacetanilide is increased as taught in U.S. Ser. No. 884,329 (noted above) to increase the rate of dye formation from a leuco dye (and make the assay more rapid), higher background levels also result.

Thus, it would be desirable to be able to increase the amount of enzyme-labeled antibody to detect low concentrations of antigen and to shorten assay time, but without adversely affecting sensitivity or increasing background.

SUMMARY OF THE INVENTION

The problems noted above are overcome with a dye-providing composition which is substantially free of peroxidase or a peroxidase-labeled specific binding species, the composition comprising an imidazole leuco dye and 4'-hydroxyacetanilide which is present in an amount up to about 2.5 mmolar.

This composition can be included in a diagnostic test kit which also comprises a peroxidase-labeled specific binding species, and a substrate for peroxidase.

Moreover, a method for the determination of a ligand comprises:

A. contacting a sample of a biological specimen suspected of containing a ligand with one or more specific binding species, at least one of which is a receptor for the ligand, and the same or a different specific binding species which is labeled with peroxidase, the labeled species being reactive with either the ligand or a receptor for the ligand, to form a peroxidase-labeled reaction product of the ligand with the specific binding species, and B. in the presence of a substrate for peroxidase, determining the labeled reaction product by contacting the reaction product with a dye-providing composition which is substantially free of peroxidase or a peroxidase-labeled specific binding species, the composition comprising an imidazole leuco dye and 4'-hydroxyacetanilide which is present in an amount up to about 2.5 mmolar.

The present invention provides a highly sensitive and accurate assay for a target ligand where an imidazole leuco dye is used as a dye-providing reagent, and peroxidase is used as the label. This assay is particularly useful for the detection of Streptococcal antigens, such as Streptococcus A antigen.

The background of the assay is kept very low in the assay while the sensitivity is increased significantly. This result was achieved by significantly lowering the amount of 4'-hydroxyacetanilide normally used with the leuco dye. For example, as described in U.S. Ser. No. 206,257 of Warren III et al (noted above), 4'-hydroxyacetanilide is used in an amount of 5 mmolar. Warren et al is following the teaching in U.S. Ser. No. 884,329 (noted above) which suggests relatively large amounts of the phenol in order to accelerate the reaction to provide dye. Until the present invention, it was believed that large amounts of phenol (for example, 4'-hydroxyacetanilide) were required to obtain a sensitive assay.

We have found, unexpectedly, that when the amount of 4'-hydroxyacetanilide is reduced from the relatively large amounts taught by the art noted above, and the amount of peroxidase-labeled specific binding species is increased, the overall kinetics of dye formation, complexation of the labeled specific binding species and sensitivity of the assay are increased without increasing the background.

This is unexpected because the art teaches the use of higher levels of 4'-hydroxyacetanilide to increase sensitivity. Moreover, the amount of peroxidase-labeled species is kept lower in the art in order to reduce background. One would expect that lower 4'-hydroxyacetanilide concentration and higher labeled species would reduce sensitivity and increase background. This did not occur with the present invention.

It was expected that a reduction of 4'-hydroxyacetanilide concentration from 5 mmolar to, for example, 0.7 mmolar, would not only slow the kinetics of dye formation unacceptably, but would also unacceptably increase assay time. This did not occur because the peroxidase-labeled species was increased in conjunction with the decrease in 4'-hydroxyacetanilide to provide a highly sensitive, rapid and low background assay. The present assay can be carried out within 10 minutes, and generally in less than 5 minutes.

DETAILED DESCRIPTION OF THE INVENTION

The present invention can be used to rapidly detect the presence of a target ligand in a biological specimen from human or animal hosts. As noted above, this ligand can be any chemical or biological substance for which there is a corresponding receptor which specifically reacts therewith to form a complex. Representative ligands include, but are not limited to, proteins (such as enzymes, antibodies, and antigenic proteins and fragments thereof), peptides, polypeptides, nucleotides, carbohydrates, plant lectins, toxins, haptens, drugs, viruses, fungi and bacteria and components thereof, and other materials known to one skilled in the art. For example, the present invention is useful for the detection of Chlamydial, Gonococcal or herpes antigens. This invention is particularly useful for the detection of Streptococcal antigens, such as the carbohydrate antigens extracted from Streptococcal A, B, C or G group organisms. Streptococcal A antigen is most particularly detectable with this invention.

Biological samples which can be so assayed include, but are not limited to, whole blood or a component (serum or plasma) thereof, saliva or mucous from the throat or mouth, lacrimal fluid, spinal fluid, feces, urine, vaginal secretions, seminal fluid, human tissue or organ extracts and human milk. The specimens can be collected using suitable procedures. For example, a throat swab specimen is generally assayed in the detection of Streptococcal antigens.

The critical aspect of this invention is the presence of up to about 2.5 mmolar of 4'-hydroxyacetanilide in a dye-providing composition comprising an imidazole leuco dye (described below), which composition is substantially free of peroxidase or a peroxidase-labeled specific binding species. By "substantially free" is meant that no more than a trace amount of peroxidase or a peroxidase-labeled material is present. The labeled species is provided for use in the assay separately (as described below).

The amount of 4'-hydroxyacetanilide used in the invention can be varied depending upon the amount of peroxidase-labeled species used in order to maximize assay sensitivity and overall kinetics and to provide low background in the assay. Preferred amounts are from about 0.5 to about 2 mmolar. A more preferred amount for use in an assay for Streptococcal A antigen is from about 0.5 to about 1 mmolar. Assays for other ligands may utilize different preferred amounts.

The leuco dye useful in the dye providing composition is an imidazole dye which is capable of providing a dye in the presence of peroxidase and a substrate therefor. The resulting dye is generally detectable in the visible region of the electromagnetic spectrum (generally from about 400 to about 700 nm). Imidazole leuco dyes useful herein are either diarylimidazole or triarylimidazole leuco dyes. Many useful compounds are known in the art, such as U.S. Pat. No. 4,089,747 (issued May 16, 1978 to Bruschi), and references noted therein, E.P. Publication 122,641 (published Oct. 24, 1984) and Japanese Patent Publication 58(1983)-045,557, all of which are incorporated herein by reference.

The triarylimidazoles having the following general structure are particularly useful:

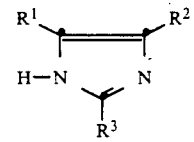

wherein $R^1$, $R^2$ and $R^3$ are independently of each other an organic group such that at least one of them is an ortho or para-hydroxy-substituted aryl group of up to 18 carbon atoms, the other two groups being aryl groups chosen such that the imidazole oxidation potential is within the range of from about $-70$ mV to about $+100$ mV as measured by cyclic voltammetry against a standard calomel electrode using a carbon based electrode Oxidation potential measurements can be made according to known electrochemical techniques (see, for example, Sawyer et al, *Experimental Electrochemistry for Chemists*, John Wiley & Sons, New York., 1974)

As used herein, the term "aryl" is meant to include aromatic hydrocarbon groups, such as phenyl, naphthyl or anthryl, tolyl, xylyl and other substituted aromatic groups. The number of carbon atoms refers to the total number of nuclear carbon atoms as well as those in substituents. At least one of the $R^1$, $R^2$ and $R^3$ groups has an ortho or para electron donating substituent such as an alkyloxy (—OR) wherein R is alkyl of 1 to 8 carbon atoms (for example, methyl, ethyl, isopropyl, t-butyl, hexyl, chloromethyl or methoxymethyl), or a dialkylamino wherein alkyl is as just defined. The $R^1$, $R^2$ and $R^3$ groups can have one or more other substituents which are electronically compatible with the imidazole nucleus to provide a suitable dye upon oxidation. Further details of useful triarylimidazole compounds are provided in U.S. Pat. No. 4,089,747 (noted above).

Particularly useful leuco dyes are selected from the group consisting of:

2-(4-hydroxy-3,5-dimethoxyphenyl)-4,5-bis(4-methoxyphenyl)imidazole, 2-(3,5-dibromo-4-hydroxyphenyl)-4,5-diphenylimidazole, 2-(3-bromo-5-methoxy-4-hydroxyphenyl)-4,5-bis(4-methoxyphenyl)imidazole, 4,5-bis(4-dimethylaminophenyl)-2-(4-hydroxyphenyl)imidazole, 4,5-bis(4-dimethylaminophenyl)-2-(4-hydroxy-3-methoxyphenyl)imidazole, 2-(4-hydroxyphenyl)-4,5-bis(4-methoxyphenyl)-imidazole, and 4,5-bis(4-dimethylaminophenyl)-2-(4-hydroxy-3,5-dimethoxyphenyl)imidazole.

The amount of leuco dye useful in the composition can be varied widely depending upon how the composition is used and the target ligand. Generally, it is present in an amount of from about $10^{-6}$ to about $10^{-3}$ molar.

The dye-providing composition can include other reagents, buffers (for example, to buffer the composition from about 4 to about 9) or chelating agents as desired. For example, it can contain a substrate for peroxidase. Generally, this is hydrogen peroxide, but other peroxides may be useful, in amounts known to one skilled in the art. In addition, the composition can include water-soluble or -dispersible polymers which stabilize the leuco dye. Such polymers are described, for example, in copending and commonly assigned U.S. Ser. No. 136,166, filed Dec. 12, 1987 by McClune and Bishop. Particularly useful polymers are selected from the group consisting of vinylpyrrolidone polymers, acrylamide polymers, acrylic and methacrylic acid polymers, polyethylene glycols and polyamines. A preferred dye-providing composition is illustrated in Example 1 below.

The assays of the present invention are carried out using a peroxidase-labeled specific binding species. This species can be any biological or chemical compound which specifically reacts with another chemical or biological compound such as a target ligand as defined above, and to which peroxidase can be attached in a suitable manner. The labeled species can be reactive with the ligand or to a receptor to the ligand. In most embodiments, the labeled species is an antibody to an antigen, or an antibody directed to another antibody. In other assays, an antigen or hapten is labeled in order to detect an antibody or antigen (as in a competitive binding assay). Representative specific binding species include, but are not limited to, antibodies, antigenic materials, peptides, polypeptides, nucleotides, haptens, drugs, hormones, avidin or derivatives thereof, biotin or derivatives thereof, lectins or derivatives thereof and others known to one skilled in the art. It would be readily apparent to a skilled worker as to what specific binding species would be useful with a particular target ligand or receptor.

The amount of peroxidase-labeled specific binding species used in an assay will vary depending upon the target ligand. Generally, however, it will be from about 1 to about 50, and preferably from about 7 to about 20, ng/ml.

As described in U.S. Ser. No. 206,257 (Warren III et al), noted above, the peroxidase-labeled specific binding species is preferably used in combination with one or more water-soluble proteins or carbohydrates, substantially none of which has a pI greater than about 5 (defined in the application).

Peroxidase-labeled species can be prepared using known procedures. Some are commercially available. Generally, the conjugate of a specific binding species and peroxidase is prepared by derivatizing the enzyme, purifying the enzyme derivative, reacting the derivative with the antibody, and purification and characterization of the resulting conjugate. A number of procedures are described in the following references: Yoshitake, *Eur. J. Biochem.*, 101, 395 (1979), Nakane et al, *J Histochemistry and Cytochemistry*, 22, 1084 (1974) and Avrameas, *Bull. Soc. Chim, Biol.*, 50, 1169 (1968).

The dye-providing composition of this invention can be used in any immunoassay wherein a peroxidase-labeled reagent is used for detecting the presence or absence, or amount of a specific binding reaction. For example, the assay could be an immunometric assay (also known as a "sandwich" assay), competitive binding, direct or indirect attachment assays, and others known to one skilled in the art. Each assay is well exemplified in the art, and requires no further description here. Useful assays can be carried out in solution, or in diagnostic test devices, analytical elements, reagent strips or other useful articles.

For exemplification purposes, the remainder of this discussion is directed to assays for ligands, such as Streptococcal antigens, using a microporous membrane as a capture and filtration means. The membrane is generally incorporated into a diagnostic test device which is capable of receiving and retaining all reagents and fluids used in the assay, but it should be understood that the invention is not limited to these specific assays or features. Reference is made to the details provided in copending and commonly assigned U.S. Ser. No. 206,257 of Warren III et al (noted above), and U.S. Ser. No. 206,236 of Snyder, Grogan and Sutton entitled "Microporous Article Having a Stabilized Specific Binding Reagent, a Method for Its Use and a Diagnostic Test Kit", both filed on even date herewith and incorporated herein by reference.

Various test devices are known in the art including those described in U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May 1, 1984 to Liotta). Particularly useful devices are described in copending and commonly assigned U.S. Ser. No. 098,248 (filed Sept. 18, 1987 by Hinckley et al) and in copending and commonly assigned U.S. Ser. No. 136,211 (filed Dec. 18, 1987 by Smith-Lewis).

More specifically, the test device comprises a water-insoluble shell having one or more test wells therein each of which can accommodate a sample of a biological specimen and appropriate reagents.

The shell can be prepared from any useful water-insoluble material such as glass, polymeric materials, ceramics, fibrous materials, cellulosic materials and other materials known in the art.

In a preferred embodiment, the test device has three test wells designed for providing a specimen test result and positive and negative control results. Each test well has a microporous article mounted therein. Another test device is described and claimed in copending and commonly assigned U.S. Ser. Nos. 019,810 (filed Feb. 27, 1987 by Hinckley) and 098,248 (filed Sept. 18, 1987 by Hinckley et al). Other variations of useful test devices would be within the purview of a worker of ordinary skill in the art.

Generally, the method of this invention is carried out by contacting a sample of a biological specimen suspected of containing a target ligand with one or more specific binding species, at least one of which is a receptor for the ligand, and the same or a different specific binding species which is peroxidase-labeled. The labeled species and ligand can be directly or indirectly complexed. They are directly complexed if the labeled species is a receptor for the ligand. Alternatively, the labeled species may be secondarily complexed with the ligand through one or more other specific binding molecules which bind to the ligand and to each other. This contact results in a peroxidase-labeled reaction product between the target ligand and the corresponding receptor molecules.

This contact can be accomplished in any suitable manner, but preferably the specimen is mixed with the species in a test device.

Prior to, simultaneously with or subsequently to this contact, the target ligand or specific binding species can be complexed with other specific binding compounds as long as this reaction does not hinder the reaction of the labeled species directly or indirectly with the ligand. In some assays, the assay is carried out with a single peroxidase-labeled receptor. In other assays, two or more receptors for the ligand are used, one of which is labeled. Such situations could involve an immunometric assay. The unlabeled receptor can be insolubilized or capable of being insolubilized at a later point in the assay. Alternatively, the assay could be a direct binding assay wherein the ligand directly attaches to a solid support, and is reacted with a labeled receptor or is reacted with an unlabeled receptor followed by reaction of the receptor with a peroxidase-labeled receptor to the first receptor.

The labeled complex formed in the assay is then detected in a suitable manner by adding the dye-forming composition of this invention which will provide a dye in the presence of peroxidase and a substrate, such as hydrogen peroxide. The resulting dye can be observed visually or measured using suitable spectrophotometric equipment.

The diagnostic test kit of this invention includes the dye-providing composition of this invention as well as a peroxidase-labeled specific binding species and a suitable peroxidase substrate. These kit components can be packaged in a suitable manner and included in a carrier of some type which can be compartmentalized to receive the vials or bottles of liquid or solid reagents. In addition, it can also include one or more of the following which are useful in carrying out the method: test device, extraction reagents (if the ligand must be extracted before the assay), wash solutions, diluents, further receptor molecules and other reagents known to one skilled in the art for a given assay. Reagents can be provided in dry form or in appropriate solutions. Nonreactive components of the kit can include instructions, mixing vessels, stirring means, pipettes and the like.

The following examples are representative of the practice of this invention but are not intended to limit it.

MATERIALS

A specific binding composition was prepared to contain an anti-Streptococcus A-peroxidase labeled conjugate, which was prepared using commercially available and immunpurified rabbit polyclonal antibodies and horseradish peroxidase from Miles Laboratories (Elkhart, Ind.) by the method described by Yoshitake et al, *Eur. J. Biochem.* 101, 395 (1979). Mixed with the conjugate (1–20 $\mu$g/ml) were succinylated casein (pI 4.5, 0.5–1.5% by weight), 0.1 molar 4-morpholinopropane sulfonic acid buffer (pH 7.5), 10 mmolar 4'-hydroxyacetanilide) and 0.01% by weight of preservative.

Succinylated casein was prepared by reacting casein with an equal weight of succinic anhydride for four hours at 25° C., then purifying the product by dialysis.

The buffers mentioned and used herein are available from a number of commercial sources including Sigma Chemical Co.

LoProdyne ® nylon microporous membranes were obtained from Pall Corp., incorporated into the test wells of a disposable test device and pretreated with Fluorad FC 135 surfactant (0.05 g/m$^2$, available from 3M Corp.).

EXAMPLE 1

Dye-Providing Composition

This example illustrates the preparation of a preferred dye-providing composition according to this invention. A leuco dye solution was prepared with 2-(4-hydroxy-3,5-dimethoxyphenyl)-4,5-bis(4-methoxyphenyl-)imidazole as follows.

Solid leuco dye (to make a 0.1% solution) was dissolved in a solution of 20% poly(vinylpyrrolidone) in sodium phosphate buffer (5 mmolar). This solution was then added to a solution containing hydrogen peroxide (10 mmolar), 4'-hydroxyacetanilide electron transfer agent (0.7 mmolar) and diethylenetriaminepentaacetic acid chelating agent (10 $\mu$molar) in sodium phosphate buffer to produce a final concentration of 1% poly(vinylpyrrolidone) and 0.005% leuco dye.

EXAMPLE 2 and 3

Comparative Assays for Streptococcus A Antigen

These examples demonstrate the use of the composition of Example 1 in the method of this invention to detect Streptococcus A antigen in a biological specimen, and compares its use to an assay wherein the amount of 4'-hydroxyacetanilide is outside the scope of the present invention, that is, the amount of U.S. Ser. No. 884,329 (noted above).

In Example 2, a conjugate composition and a leuco dye composition of this invention were used in comparison with conjugate and dye compositions of U.S. Ser. No. 884,329 (Control) at various conjugate incubation times.

Streptococcus A antigen was obtained from Group A strep cultures using a standard nitrous acid extraction wherein aqueous sodium nitrite was mixed with an acidic coreagent prior to the addition of the cultured organism. The extraction fluid was then neutralized by the addition of excess buffer. The Group A carbohydrate antigen was obtained using acidic ethanol and acetone, discarding the supernatant and resuspending the pellet in 0.85% saline solution. The concentration of rhamnose was determined by the method of Dische and Shattles, *J. Biol. Chem.* 175, 595–603 (1948). This concentration was resuspended in the extraction reagents comprising citric acid (10 μl, 1.2 molar), sodium nitrite solution (120 μl, 8 molar) and 4-morpholinopropane sulfonic acid buffer (120 μl, 2 molar, pH 8) in 75 mmolar ethylenediaminetetraacetic acid.

A microporous membrane as described above was incorporated into each of the three test wells of two disposable test devices which were similar to that described in U.S. Ser. No. 098,248 (noted above). A dispersion of the specific binding reagent comprising poly[styrene-co-m & p-(2-chloroethylsulfonylmethyl)-styrene] beads [2 μl of a 1% solid suspension containing 5%, by weight, poly(acrylamide) in glycine (0.1 molar, pH 8.5) and 0.0005%, by weight, of an optical brightener], was added to the center area of the membrane in the test well identified as the specimen test well. To the beads were covalently bound immunopurified rabbit polyclonal antibodies to Streptococcus A antigen.

A second test well, considered the negative control well, contained a dried dispersion (2 μl) of the same polymeric beads to which had been attached rabbit gamma globulin (1%, by weight) admixed with poly(acrylamide) (5% by weight in glycine buffer) and the optical brightener. This dispersion was applied in a center area of the membrane.

A third test well, considered the positive control well, contained a dried dispersion of the reagent (2 μl) described above in poly(acrylamide) (5% by weight in glycine buffer), the optical brightener and 20 ng/ml of the Streptococcus A antigen. This dispersion was applied in a center area of the membrane.

Two-hundred μliters of the antigen extract solution (0.62 ng/ml) was added to the specimen test well only and allowed to flow through.

A first solution (40 μl) containing the conjugate described above (5 μg/ml), and a second solution (40 μl) containing the same conjugate (15 μg/ml) were added to separate disposables and allowed to drain through the membrane.

The disposables were then incubated at room temperature for 30, 60 and 120 seconds.

A wash solution containing sodium decyl sulfate (70 mmolar) in sodium phosphate buffer (0.1 molar, pH 7.2) was applied to all wells and allowed to drain through the membrane.

A dye-providing composition (120 μl) containing the leuco dye composition described above with 5 mmolar 4'-hydroxyacetanilide and identified herein as the Control, was added to test wells containing the first conjugate solution. A dye-providing composition (120 μl) of this invention containing the same dye and 0.7 mmolar 4'-hydroxy-acetanilide was added to test wells containing the second conjugate solution. Each composition was allowed to drain through the membrane.

The disposables were then incubated at room temperature for 2 minutes and the dye formed on the membrane was measured by reflectance and converted to transmission density ($D_T$). The results are shown in Table I below.

TABLE I

| Conjugate Incubation Time (sec.) | $D_T$ Control 5 μg/ml: 5 mmolar* | $D_T$ Invention 15 μg/ml: 0.7 mmolar* |
| --- | --- | --- |
| 30 | 0.007 | 0.007 |
| 60 | 0.019 | 0.024 |
| 120 | 0.026** | 0.073** |

*Conjugate Amount: 4'-Hydroxyacetanilide Amount
**Background = 0.007

These results indicate that the present invention gives a more rapid assay because shorter incubation times (that is, 60 seconds) are required to obtain about the same signal as the Control. Moreover, after two minutes of incubation, the present invention showed the same low background as the Control but had considerably higher sensitivity.

In Example 3, dye incubation times were varied. The procedure of Example 2 was repeated except that the antigen concentration was 2.5 ng/ml, the amount of conjugate used in the Control assay was 3 μg/ml versus 9 μg/ml in the invention assay, a 2 minute incubation period before the wash step was used, and dye incubation for 30, 60 and 120 seconds was carried out at room temperature after the wash step. The results of the assays are shown in Table II below.

TABLE II

| Dye Incubation Time (sec.) | $D_T$ Control 3 μg/ml: 5 mmolar* | $D_T$ Invention 9 μg/ml: 0.7 mmolar* |
| --- | --- | --- |
| 30 | 0.022 | 0.026 |
| 60 | 0.027 | 0.057 |
| 120 | 0.073** | 0.114** |

*Conjugate Amount: 4'-Hydroxyacetanilide Amount
**Background = 0.007

These results indicate that the present invention provides a more rapid assay because shorter incubation times (that is 60 seconds are required to obtain a high signal, as opposed to 120 seconds for the Control assay. Moreover, after two minutes of incubation, the present invention showed the same low background as the Control but had considerably higher sensitivity.

The invention has been described in detail with particular reference to preferred embodiments thereof, but it will be understood that variations and modifications can be effected within the spirit and scope of the invention.

We claim:

1. A method for the determination of a ligand, said method comprising:
    A. contacting a sample of a biological specimen suspected of containing a ligand with:
        a specific binding species which is a receptor for said ligand,
        and the same or different specific binding species which is labeled with peroxidase, said labeled species being reactive with either said ligand or a receptor for said ligand,
        to form a peroxidase-labeled reaction product of said ligand with said specific binding species which is captured on a microporous membrane, and
    B. after the formation and capture of said peroxidase-labeled reaction product, and in the presence of a substrate for peroxidase, determining said labeled reaction product by contacting said reaction product on said membrane with an aqueous dye-providing composition which is substantially free of peroxidase or a peroxidase-labeled specific binding species, said composition comprising an imidazole leuco dye, 4'-hydroxyacetanilide which is present in an amount of from about 0.5 to about 2.5 mmolar, and a water-soluble or -dispersible polymer selected from the group consisting of vinylpyrrolidone polymers, acrylamide polymers, acrylic and methacrylic acid polymers, polyethylene glycols and polyamines as a determination of said ligand.

2. The method of claim 1 for the determination of Streptococcus A antigen.

3. The method of claim 1 for the determination of a Chlamydial, Gonococcal or herpes antigen.

4. The method of claim 1 wherein said ligand receptor is peroxidase-labeled.

5. The method of claim 1 wherein said ligand is reacted with at least two receptors, one of which is peroxidase-labeled.

6. The method of claim 1 wherein said ligand is reacted with an unlabeled receptor, and said peroxidase-labeled species is reactive with said unlabeled receptor only.

7. The method of claim 1 wherein said leuco dye is a triarylimidazole represented by the formula:

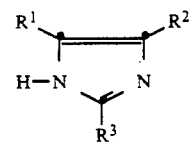

wherein $R^1$, $R^2$ and $R^3$ are independently an organic group such that at least one of them is an ortho or para-hydroxy-substituted aryl group of up to 18 carbon atoms, the other two groups being aryl groups chosen such that the imidazole oxidation potential is within the range of from about $-70$ mV to about $+100$ mV as measured by cyclic voltammetry against a standard calomel electrode using a carbon based electrode.

8. The method of claim 1 wherein said peroxidase substrate is hydrogen peroxide.

* * * * *